United States Patent
Khevenhuller Metsch

(10) Patent No.: US 10,980,709 B2
(45) Date of Patent: Apr. 20, 2021

(54) DEVICE FOR RECONSTITUTING AND ADMINISTERING DRUGS

(71) Applicant: Johannes Franziskus Khevenhuller Metsch, Rome (IT)

(72) Inventor: Johannes Franziskus Khevenhuller Metsch, Rome (IT)

(73) Assignee: GEXIT S.R.L., Rome (IT)

(*) Notice: Subject to any disclaimer, the term of this patent is extended or adjusted under 35 U.S.C. 154(b) by 529 days.

(21) Appl. No.: 15/573,286

(22) PCT Filed: May 13, 2016

(86) PCT No.: PCT/IB2016/052772
§ 371 (c)(1),
(2) Date: Nov. 10, 2017

(87) PCT Pub. No.: WO2016/181356
PCT Pub. Date: Nov. 17, 2016

(65) Prior Publication Data
US 2018/0092809 A1    Apr. 5, 2018

(30) Foreign Application Priority Data
May 14, 2015    (IT) .................. 102015000015094

(51) Int. Cl.
*A61J 1/20* (2006.01)
*A61J 1/10* (2006.01)
(Continued)

(52) U.S. Cl.
CPC .............. *A61J 1/2089* (2013.01); *A61J 1/10* (2013.01); *A61J 1/1406* (2013.01); *A61J 1/201* (2015.05);
(Continued)

(58) Field of Classification Search
CPC ........ A61J 1/2089; A61J 1/201; A61J 1/2055; A61J 1/10; A61J 1/1406; A61J 1/1487; A61M 2039/222
(Continued)

(56) References Cited

U.S. PATENT DOCUMENTS 5,342,346 A    8/1994    Honda et al.
5,352,191 A    10/1994   Sunago et al.
(Continued)

FOREIGN PATENT DOCUMENTS

| AU | 2002301321 B2 | 6/2005 |
| EP | 0565103 A1 | 10/1993 |
| WO | 2010127691 A1 | 11/2010 |

OTHER PUBLICATIONS

International Search Report for PCT/IB2016/062772 dated Aug. 16, 2017.

*Primary Examiner* — Andrew J Mensh
(74) *Attorney, Agent, or Firm* — Abelman, Frayne & Schwab; Stefan Knirr

(57) ABSTRACT

Device (100) for reconstituting an active ingredient in sterile powder, comprising a vial (4) containing the active ingredient; a flexible bag (1) containing a sterile liquid; a connecting component (5) secured to the vial (4) and to the flexible bag (1); an elastomeric sealing ring (10) arranged between the connecting component (5) and the vial (4), an axially perforated spike (7), constrained to the connecting component (5), wherein a sterile chamber (70) is provided, delimited by the vial (4), by the connecting component (5) and by the sealing ring (10, 110), whereby the active ingredient is reconstituted in sterile conditions.

10 Claims, 6 Drawing Sheets

(51) Int. Cl.
*A61J 1/14* (2006.01)
*A61M 39/22* (2006.01)
(52) U.S. Cl.
CPC ............ *A61J 1/2055* (2015.05); *A61J 1/1487* (2015.05); *A61M 2039/222* (2013.01)
(58) Field of Classification Search
USPC .......................................................... 604/408
See application file for complete search history.

(56) References Cited

U.S. PATENT DOCUMENTS

| | | | | | |
|---|---|---|---|---|---|
| 5,380,315 | A | * | 1/1995 | Isono | A61J 1/2089 604/403 |
| 2012/0330267 | A1 | * | 12/2012 | Domkowski | A61J 1/2089 604/414 |

* cited by examiner

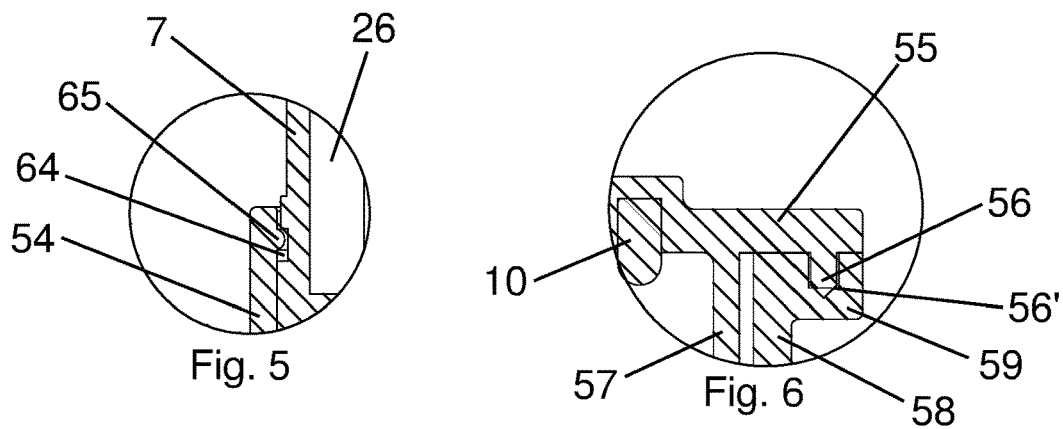
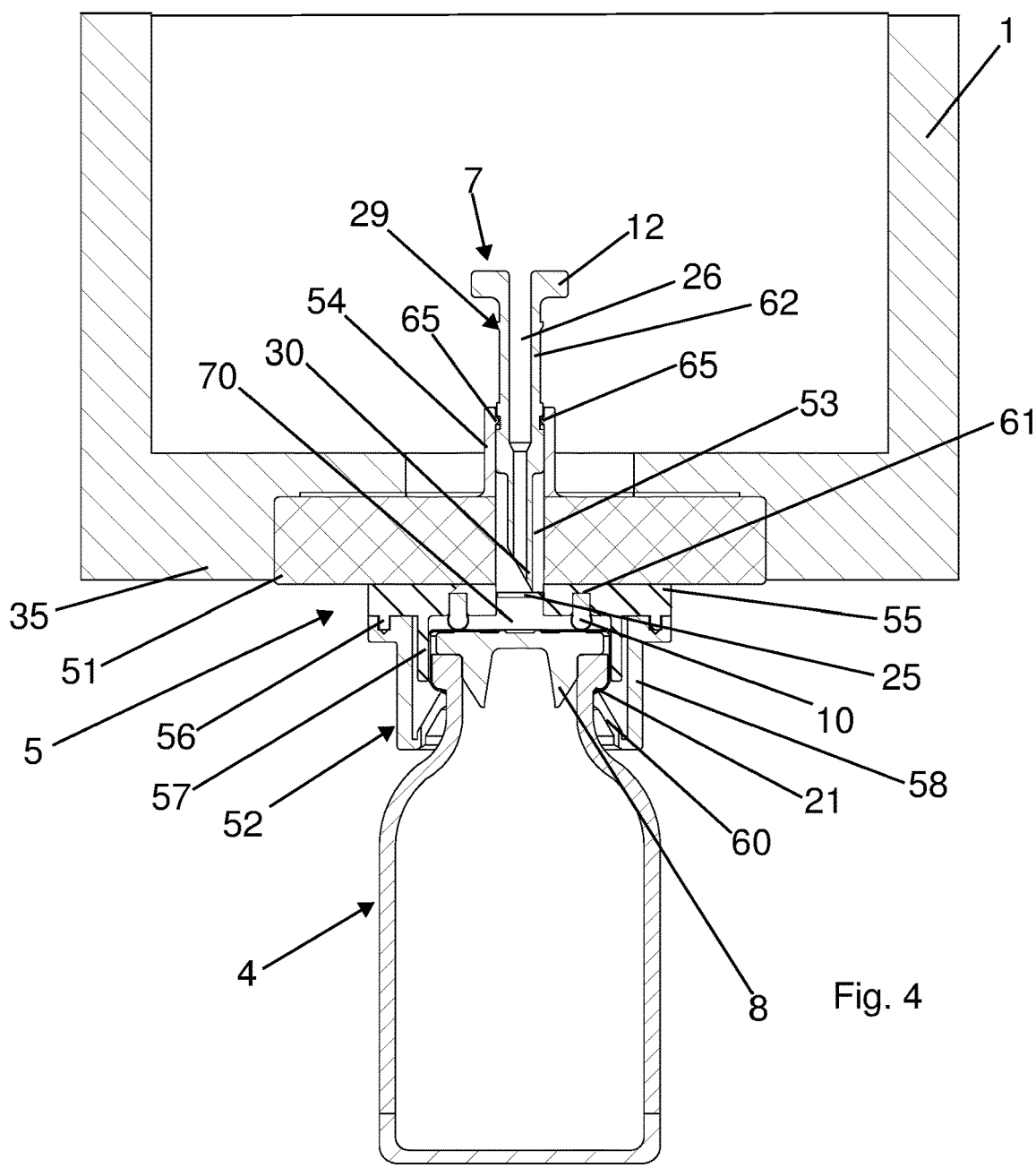

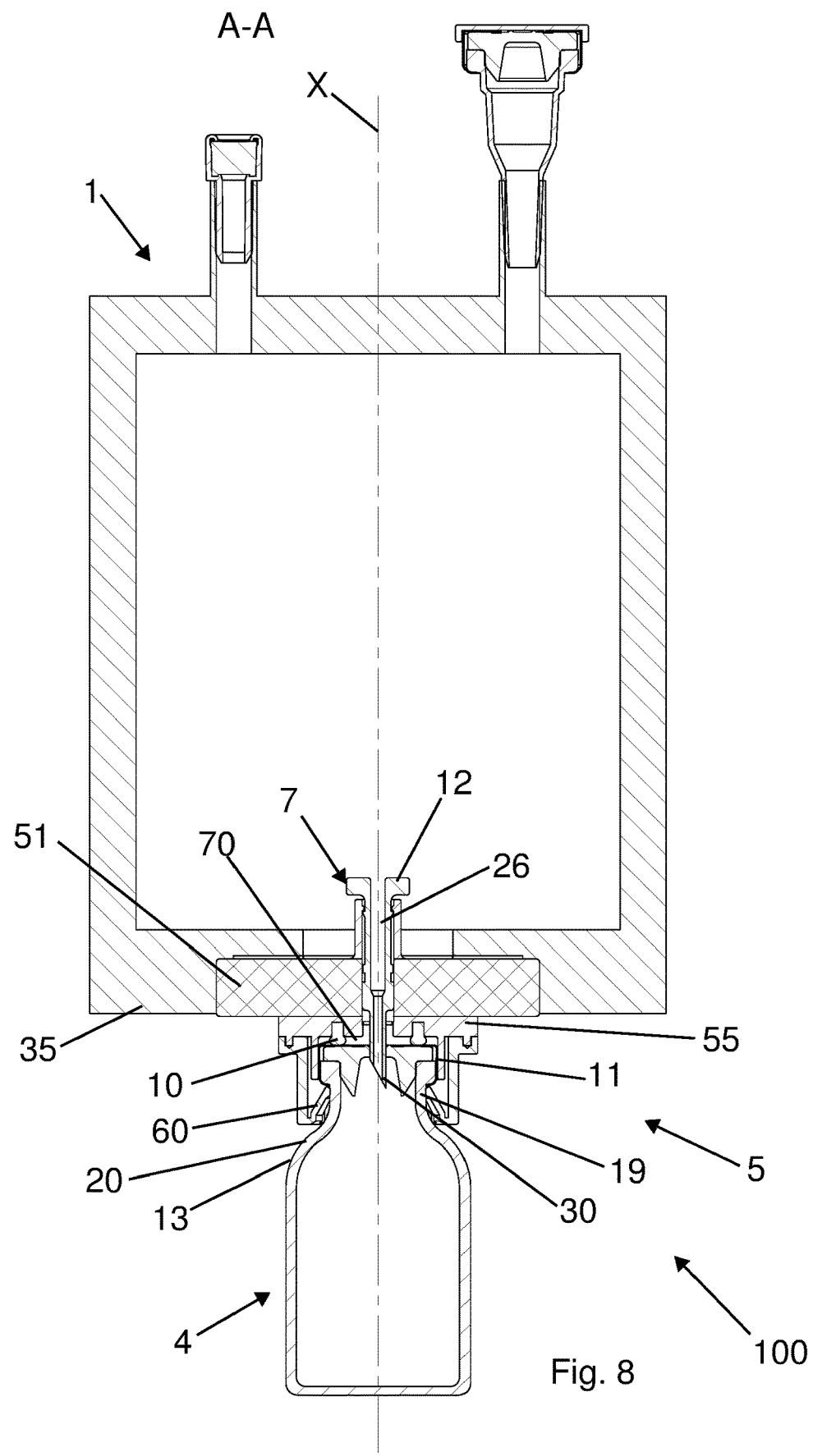

DEVICE FOR RECONSTITUTING AND ADMINISTERING DRUGS

RELATED APPLICATIONS

This application is a national phase of International Application No. PCT/IB2016/052772 filed May 13, 2016, and claims priority from Italian Patent Application No 102015000015094 filed May 14, 2015, both incorporated by reference in their entirety.

FIELD OF THE INVENTION

The present invention relates to a device for reconstituting and administering drugs, especially drugs in the form of sterile powder contained in a vial and reconstitutable with a sterile diluent contained in a flexible bag; the invention also relates to a process for the production of the device.

BACKGROUND ART

Some injectable drugs are not stable in solution. For this reason, they are sold in the form of sterile powder contained in an internally sterile vial. The reconstitution of the drug in solution should be prepared immediately before administration by properly trained personnel. Usually, the reconstituted product has a much reduced expiration which may last from a few hours up to two days at room temperature and up to 4 days at refrigerated temperatures. It is therefore advisable to administer freshly reconstituted solutions.

The sterile diluent for reconstitution is often contained in flexible bags which may have different volumes, and which must be internally sterile. Examples of suitable diluents are water (Water For Injection), saline solution (NaCl 0.9%), dextrose or others.

Currently, in order to reconstitute the powdered drug, an operator must go to a clean—but not sterile—environment and introduce the sterile diluent (contained in the bag) into the vial containing the drug, following a specific procedure.

Vials are glass or fiberglass containers suitably closed with a cap pierceable by a needle and sealed with an aluminum cover which has a removable portion, also known as flip-off. The vial filling process takes place in the factory under sterile conditions, and is performed in appropriate cleanrooms.

The flexible bags are substantially containers of polypropylene or a similar material, which are filled with an ultra-filtered diluent and sterilized by steam autoclaving.

For intramuscular (IM) administration via a syringe, the reconstitution procedure requires the user to withdraw the sterile diluent from a flexible bag using a syringe, inject it into the vial containing the drug using the syringe and withdraw the reconstituted solution using a syringe for IM administration.

In the case of intravenous administration (IV) by infusion, a connector is usually used for connecting the vial and flexible bag, also known as binary connector, consisting of a pin, or spike, with two tips. Two opposite ends of the connector are shaped to couple to the vial and to the flexible bag, respectively, after the pin has passed through the cap of the vial and the closure of the exit port of the flexible bag, respectively. The reconstituted solution is returned into the flexible bag and is administered through a dedicated infusion tubing directly into a vein.

These operations are disadvantageously subject to drawbacks. In particular:

risk of contamination, since the reconstitution takes place in a clean but non-sterile environment and the solution comes into contact with non-sterile components;

risk of reconstitution errors, since a wrong diluent may be used, such as a bag containing a diluent and/or a volume of diluent other than necessary;

risk of personal injury, due to exposed tips that involve risks of injuries or accidental stings by the operators;

risk of degradation of the active ingredient, if the administration of the drug does not take place in a short time. This happens for example in cases where the solutions are reconstituted in hospital pharmacies, which are places dedicated to the so-called compounding but when ready for administration must reach the department or the patient's home.

Examples of connectors, or binary connectors, for the reconstitution of solutions for IV use are described in AU 2002 301 321 B2 and ER 0565 103 A1.

These documents describe connectors specifically designed to be connected to the vial and to the bag in hospital or at home. The connector is provided individually in a packaging, and must necessarily be manipulated by an operator to make the connection to the vial and the bag. In particular, the packaging that contains the binary connector is intended to be opened in an environment which, although clean, is not sterile. It is clear that hospital environments in which the procedures for the reconstitution of injectable solutions are carried out are not comparable to the sterile environments that the industry must use to maximize the quality of both the powdered drug and of the diluent.

Therefore, the use of this type of connectors does not ensure the required sterility. In particular, the connection zones with the vial and with the bag cannot be sterile during the operation of connection to the vial and to the flexible bag. Moreover, known connectors require an assembly procedure prior to reconstitution that is too complex, have high production costs and, as said, do not ensure the system sterility. Therefore, some types of known connectors do not meet the quality standards that should be respected.

Other known solutions involve incorporating the entire vial into a further container. In this way, however, the complexity of the device is increased and the possibility of verifying the correct dissolution of the substance, which is an important check to carry out on the solution to verify the absence of external particles, is reduced.

Finally, the connectors are often very delicate and, therefore, subject to breakage in particular during the user's handling and transport and do not ensure a correct piercing of both elements to be perforated, that is to say, of the vial cap and of the flexible bag.

Therefore, a need is felt to provide a device for reconstituting and administering powdered drugs and a process for its production, which allows overcoming the aforesaid drawbacks.

SUMMARY OF THE INVENTION

An object of the present invention is to provide a device for reconstituting and administering a powdered drug which ensures the sterility of the solution containing the drug reconstituted with a diluent.

Another object of the present invention is to provide such a device which allows simplifying the compounding step, i.e. the reconstitution of the drug for administration, while preventing risks due to human error.

The present invention, therefore, achieves these and other objects by providing a device for reconstituting an active ingredient in the form of powder, which according to claim 1 comprises:

a vial containing said active ingredient as sterile powder, having a mouth and a pierceable closing member which closes the mouth;

a flexible bag containing a sterile liquid;

a connecting component fixed to the vial and to the flexible bag;

an elastomeric sealing ring arranged between the connecting component and the closing member of the vial, an axially perforated spike, constrained to the connecting component and adapted to pierce the closing member, said spike comprising a tip, facing towards the closing member, and a head opposite to the tip, wherein there is provided a sterile chamber, delimited by the closing member, by the connecting component and by the sealing ring, wherein the spike is adapted to slide from a rest position inside the flexible bag to a working position, crossing the sterile chamber and piercing the closing member when a pressure is exerted on the head with at least one finger of a hand, allowing the passage of the sterile liquid from the flexible bag to the vial, and of the reconstituted active ingredient from the vial to the flexible bag, whereby the active ingredient is reconstituted in sterile conditions.

According to another aspect, the invention also provides a process according to claim 13 or 14 for obtaining such a device.

The presence of the sterile chamber, which is an empty space between the vial and the connecting component, is a great advantage compared to the prior art. The positioning of a sealing ring, or O-ring, between the head of the vial and the connecting component allows maintaining the appropriate sterile conditions of such a chamber. In order to open the connection between the flexible bag and the vial, it is sufficient to press on the head of the spike from outside the flexible bag in the direction of the vial. This is possible due to the flexibility of the bag, and to facilitate the operation it is preferable that the spike head, which is opposite to the tip, is enlarged with respect to the rest of the spike.

Advantageously, the invention provides a single device which comprises the vial containing the drug and the bag containing the diluent assembled to each other by means of the connecting component.

With the device of the invention, continuity is given to the efforts of the industry which produced the components for the administration of powdered drugs in compliance with GMP (Good Manufacturing Practice). In fact, the device of the invention ensures the sterility of the drug and of the solution both during the reconstitution procedure and after, even if the reconstitution is carried out in a non-sterile environment. In fact, as mentioned, the presence of the sterile chamber between the connecting component and the vial allows maintaining sterility during the reconstitution of the drug, and of the solution once it has been reconstituted.

Moreover, a greater ease of use is provided compared to the prior art, and the medical personnel may administer a freshly reconstituted drug to the patient, minimizing the time that elapses between the reconstitution and the administration, and therefore the degradation of the drug in solution prior to administration.

Another advantageous aspect of the present invention is that a stable and secure attachment is ensured between the flexible bag and the vial, even during the operator's handling.

Moreover, with the device of the invention it is not necessary to incorporate the vial into a casing.

Other advantages of the device of the invention reside in the elimination of the risk of dosing errors of the amount of diluent for reconstitution—since the bag contains a predetermined amount of liquid—and of the risks of accidental stings to the user. Since the vial and flexible bag are connected in a substantially inseparable manner, the risk of combining two components incompatible with each other is eliminated and the possibility that the device has been forced appears clearly.

Advantageously, the vial is substantially of conventional type and is produced following the standards in force.

Preferably, the connecting component between the vial and the flexible bag is sufficiently transparent, so as to allow the visual inspection of the coupling with the vial and the correct placement of the spike. To this end, it is also preferable that the spike is made of a color that is clearly visible through the connecting component. For example, the connecting component may be of sufficiently transparent white color and the spike may be red.

The dependent claims describe preferred embodiments of the invention.

BRIEF DESCRIPTION OF THE FIGURES

Further features and advantages of the invention will appear more clearly from the detailed description of preferred, but not exclusive, embodiments of a device for reconstituting and administering a drug according to the present invention, shown by way of a non-limiting example with the aid of the accompanying drawings, in which:

FIG. 4 shows a detail of FIG. 3;

FIG. 5 shows an enlarged detail of FIG. 4;

FIG. 6 shows another enlarged detail of FIG. 4;

FIG. 8 shows section A-A of the device in FIG. 1 in working position;

The same reference numerals in the figures identify the same or equivalent elements and components.

DETAILED DESCRIPTION OF AN EMBODIMENT OF THE INVENTION

Figures 1, 2:
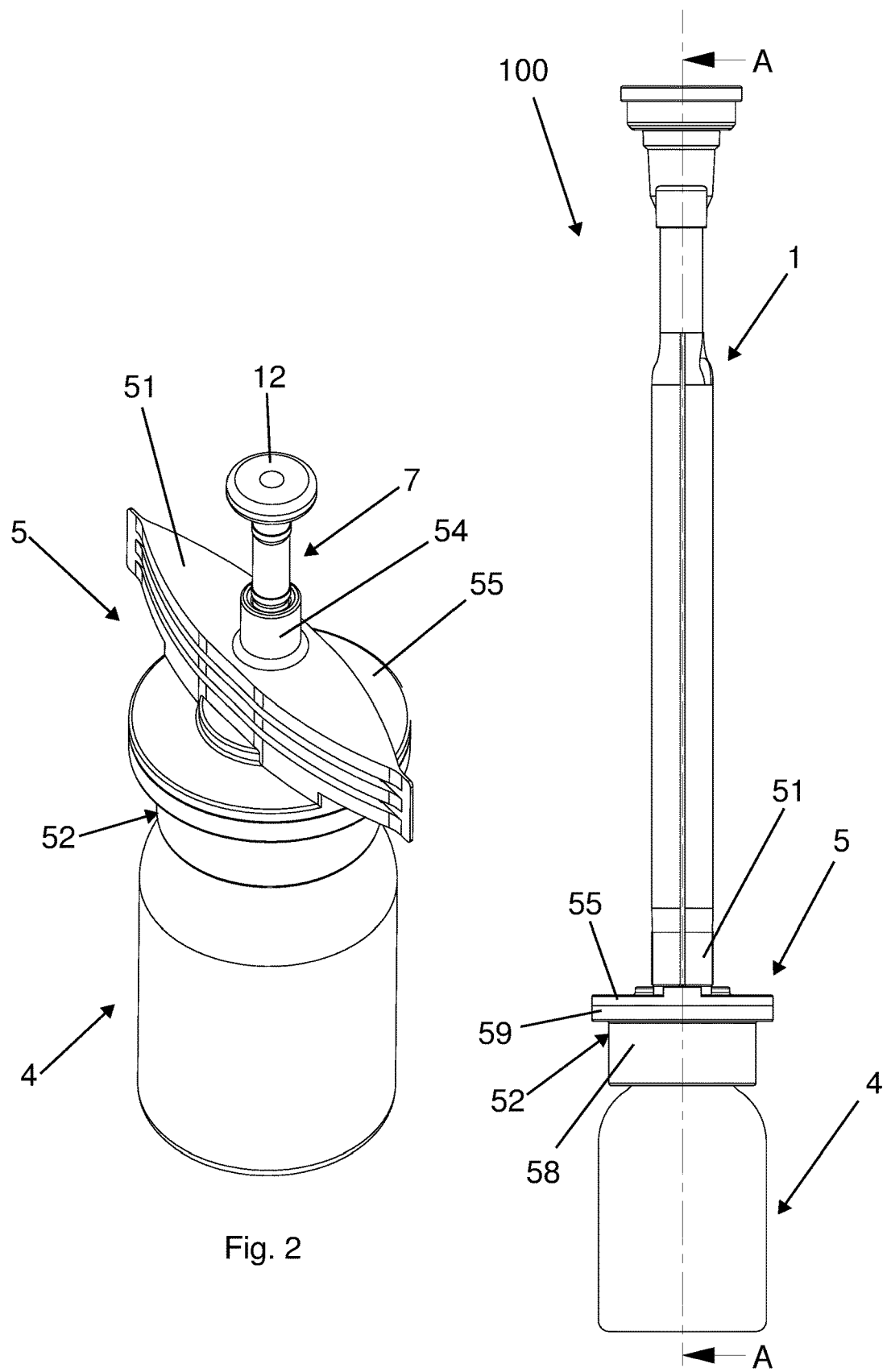
FIG. 1 shows a lateral view of a device of the invention according to a first embodiment.
FIG. 2 shows a perspective view of some components of the device in FIG. 1.

With reference to FIGS. 1 to 8, a first embodiment of a device 100 for reconstituting a drug, or active ingredient, provided in the form of powder, is shown. The device is also adapted to the administration of the reconstituted drug. Typically, the reconstituted drug is administered into a vein or muscle.

Device 100 comprises:
- a sterile vial 4, containing the drug in powdered sterile form, capped by a closing element 8, or cap 8, and sealed by a sealing member 11, or seal 11;
- a flexible bag 1; also referred to as diluent bag 1, which contains a sterile diluent suitable for reconstituting the powdered drug;
- a connecting component 5 attached to vial 4 and to the flexible bag 1,
- a spike 7, or pin or needle, adapted for the passage of diluent from the flexible bag 1 to the vial 4, and vice versa;
- a sealing ring 10, such as an O-ring 10, attached between the connecting component 5 and the sealing member 11.

Vial 4 is of conventional type, complying with the industry regulations for the storage and administration of drugs. In particular, vial 4 corresponds to the current standard and is filled with the drug according to the GMP standards in force. Vial 4, made of glass or synthetic material, has a mouth 9 which delimits an opening, and a shoulder 13 adjacent to the substantially cylindrical part of vial 4. A neck 19, preferably cylindrical, is provided between mouth 9 and shoulder 13. The radial extension of mouth 9 is greater than the radial extension of neck 19, so that a annular step 21 is present on the outer surface of vial 4, between mouth 9 and neck 19. Moreover, a transition zone 20 tapered towards mouth 9 is provided between neck 19 and shoulder 13. In particular, the transition zone 20 is substantially formed by a curved surface. The opening of mouth 9 is closed by a closing member 8 which is adapted to be pierced by the spike 7, and which is preferably a cap 8 of rubber, such as chlorobutyl or bromobutyl. Cap 8 is in abutment against mouth 9. Vial 4 is further provided with a sealing member 11, or seal 11, made for example of aluminum or other suitable material, which serves for pressure-fixing cap 8 onto vial 4 and for ensuring the sterility of the interior of vial 4. The sealing member 11 covers cap 8 and mouth 9 and is firmly attached to the latter being anchored to step 21. In particular, the sealing member 11 has a portion that follows the profile of step 21. The sealing member 11, has an open central portion, so as to leave a central portion 71 of the upper surface of cap 8 uncovered.

The flexible bag 1 contains a predetermined amount of sterile diluent fluid in its interior for reconstituting the powdered drug. The diluent may be of any type commonly used for this purpose, such as dextrose, saline solution (such as 0.9% NaCl) or water (WFI). Preferably, the flexible bag 1 is made of transparent polymeric material, so as to allow the inspection of its contents, and suitable for containing liquids to be administered to a human being. Non-limiting examples of suitable materials are polyvinyl chloride, in particular without phthalates, polyethylene, polypropylene, polyurethane, ethylene vinyl acetate and the like. The flexible bag 1 is provided with at least one port 2, 3 for the administration of the reconstituted drug with the diluent and/or for the addition of further drugs or solutions. Preferably, the flexible bag 1 is provided with two ports 2, 3 suitably sealed, of which one port 2, or spike port, for transfusion spikes, and one port 3, or needle port, for syringe needles, well-known in the industry.

The connecting component 5 and the flexible bag 1 are secured together, preferably by welding. The welding ensures that flexible bag 1 and the connecting component 5 are inseparable, and a possible separation between them would result in the breaking of the flexible bag 1.

More in detail, the connecting component 5 has an upper portion 51 welded to the flexible bag 1, and a lower portion 52 attached to the vial 4.

The upper portion 51 is at least partially incorporated in the flexible bag 1. The lateral surface of the upper portion 51 is welded to the inner side of the flexible bag 1, in particular, to the inner side of the lower edge 35.

A rigid tubular collar 54, which is integral to the connecting component 5, extends from the upper portion 51 protruding upwards. The tubular collar 54 is arranged inside the flexible bag 1 and delimits a hole 53 passing through the upper portion 51. Hole 53 is aligned with the uncovered central portion 71 of the cap 8 of the vial 4.

A plate 55, for example of circular shape, which is also traversed by hole 53, extends from the upper portion 51, in particular from the end opposite to that from which the tubular collar 54 extends. A sealing membrane 25 is provided in the hole 53 portion delimited by plate 55.

Plate 55 has an annular projection 56 which engages in a respective annular recess 56' of the lower portion 52, the annular projection 56 and the annular recess 56' being attached to each other, for example by welding (FIG. 6). Plate 55 also has another annular projection 57, radially more internal with respect to the annular projection 56. The annular projection 57 is advantageously in contact with the lateral surface of seal 11. Even more inside, an annular seat 61, or annular groove, is formed in which the elastomeric sealing ring 10, preferably made of chlorobutyl or bromobutyl, is partially accommodated. In general, it is preferable that the sealing ring 10 is made of a material suitable for contacting the diluent and the reconstituted solution. The sealing ring 10 may simply be inserted in the annular seat 61 and bound to the latter by friction; alternatively, the fixing may be achieved with an appropriate glue.

Advantageously, a hermetically sealed sterile chamber 70 is provided between the connecting component 5 and the vial 4, laterally delimited by the sealing ring 10. Preferably, the sealing ring 10 is in contact with the upper surface of seal 11, although it is contemplated that it may be in contact with the central portion of cap 8.

More in detail, the sterile chamber 70, which is an empty space, is delimited at the top by the sealing membrane 25 and by the connecting component 5, in particular by a portion of the lower side of plate 55, laterally by the sealing ring 10, and at the bottom by a part of the upper side of seal 11 and by the uncovered central portion 71 of cap 8.

The presence of the sterile chamber 70 is a big advantage. Indeed, due to the sterile chamber 70, the sterile spike 7 maintains its sterile condition after having pierced both the sealing membrane 25 and cap 8. This ensures that the procedure for reconstituting the drug always takes place under sterile conditions, thus obtaining a reconstituted drug that is sterile.

The upper portion 51 has an extension along an axis perpendicular to axis X (FIG. 3) which is greater than the extension of plate 55 and of the lower portion 52, so that the upper portion 51 projects laterally, for example from two sides, with respect to the lower portion 52. In this way, the upper portion 51 provides two gripping zones, each for one finger of the hand. The two fingers can in fact be positioned at the lower surface of the upper portion 51. Therefore, device 100 can be easily gripped and used by an operator.

Preferably, the upper portion 51 extends along the lower edge 35 of the flexible bag 1 by a length comprised between 60% and 100% of the extension of the lower edge 35. This provides an optimal grip since the gripping zones are sufficiently large.

The lower portion 52 comprises a substantially cylindrical wall 58, having a larger inner diameter than the annular projection 57, surrounding it. A crown 59, in which the annular recess 56' welded to the annular projection 56 of plate 55 is formed, radially extends outwardly from the upper end of the cylindrical wall 58 (FIG. 6). A plurality of coupling teeth 60 extend from the lower end of the cylindrical wall 58, internally to the cylindrical wall 58, forming an attachment portion. The coupling teeth 60, which in this embodiment are six, are inclined from the bottom upwards towards the interior of the cylindrical wall 58. Moreover, the coupling teeth 60 are flexible, so as to allow the snap-fitting of vial 4 into the connecting component 5. The attachment to vial 4 occurs since the connecting component 5 is designed so that the coupling teeth 60 are in abutment against the sealing portion 11 that covers step 21 of vial 4.

In other words, with an insertion movement of vial 4 into the connecting component 5, or vice versa, the coupling teeth 60 widen slightly, by deforming elastically, so as to allow the insertion and attachment of vial 4 to the connecting component 5. Once such an attachment has occurred, the connecting component 5 and vial 4 are not separable from each other with an axial separation movement. In this embodiment, the flexible teeth 60 have one end attached to the cylindrical portion 68 and one free end, so as to be able to bend.

The connecting component 5 is also designed so that by means of said attachment of the connecting component 5 to vial 4, the sealing ring 10 is subjected to compression, so as to ensure the tightness of the sterile chamber 70.

The connecting component 5 is made of plastic, preferably of the same material of which the flexible bag 1 is made, and it is preferable that it has a certain degree of transparency.

Spike 7 or pin, comprises a head 12 and only one tip 30, arranged at mutually opposite ends. Spike 7 is arranged with tip 30 facing towards vial 4 and is coaxial with the uncovered central portion 71 of cap 8.

A body 29 extends from head 12, having a smaller outer diameter than head 12. In particular, the body 29 comprises a portion 62 adjacent to head 12 and another portion 63 adjacent to portion 62. Portion 63 comprises the tip 30 and preferably has a smaller outer diameter than portion 62. Spike 7 is arranged within the flexible bag 1. In particular, a part of portion 62 is inserted into the tubular collar 54. The outer surface of portion 62 is in contact with the inner surface of the tubular collar 54, so as to provide stability to spike 7. An annular groove 64 is formed on the outer surface of portion 62. An annular projection 65 is provided on the inner surface of the tubular collar 54, accommodated in the peripheral groove 64 of the spike 7. In this way, undesired axial movements of spike 7 are prevented while the axial sliding of spike 7 is allowed when a pressure is exerted on head 12 with a finger of the hand.

Spike 7 is provided with an axial hole 26, or lumen, so as to define an axial passage for the diluent and for the solution containing the drug reconstituted with the diluent. Spike 7 defines a longitudinal axis X substantially perpendicular to the base of vial 4.

Head 12, which is the largest portion 12 of spike 7, serves for supporting a finger, such as the thumb, for pushing the spike through membrane 25, and through cap 8 into vial 4, thereby opening a two-way flow of the diluent towards the interior of vial 4 and then of the solution again into the flexible bag 1.

Preferably, spike 7 is made of plastic, such as polycarbonate. Moreover, it is also preferable that spike 7 is made of a color that is clearly visible through the connecting component 5. For example, the connecting component may be of sufficiently transparent white color and the spike may be red.

With reference to FIGS. 9 to 12, a second embodiment of a device 200 according to the invention is shown.

Vial 4 and the flexible bag 1 are substantially equal to those provided in the first embodiment, and therefore will not be described further.

Also in this embodiment, the lower edge 35 of the flexible bag 1 is welded along the outer lateral surface of the upper portion 151, or upper edge 151 of the connecting component 105.

The connecting component 105, made of preferably transparent rigid plastic, is provided with a tubular collar 124 which delimits a central opening 128 in which spike 107 is inserted. The tubular collar 124 is at the uncovered central portion 71 of cap 8, i.e. the upper surface portion of cap 8 not covered by the sealing member 11. A closing membrane 125 adapted to be pierced by spike 107 is provided in the tubular collar 124.

The connecting component 105 is provided with an attachment portion 114 to vial 4. The attachment portion 114 comprises a cavity 115 which has a first zone, proximal to the flexible bag 1, and a second zone, with at least one flexible coupling member 116 therein, adapted to be snap-fitted to mouth 9, and in particular below step 21 of vial 4, by an axial insertion movement of vial 4. This embodiment may also contemplate more than one flexible coupling member, for example a plurality of coupling teeth.

The first zone is cylindrical and is adapted to receive cap 8 sealed by the sealing member 11 and the lateral surface of mouth 9. A sealing ring 110, or elastomeric O-ring 110, is provided in the first zone, fixed between the upper surface of the sealing member 11 and the connecting component 105. The O-ring 110 may be fitted, for example by the pressure exerted by the elements between which it is interposed, or it may be fixed by a non-toxic glue or by welding to the connecting component 105.

The second zone of cavity 115 is distal from the flexible bag 101 and comprises inside the at least one flexible coupling member 116. The flexible coupling member 116 protrudes radially inwardly with respect to the cylindrical wall of the first zone of cavity 115; moreover, the at least one flexible coupling member 116 is shaped to fit the profile of neck 19 and of the transition zone 20. More in detail, the flexible coupling member 116 is shaped as a circumferential tooth with the profile of the inner surface facing towards vial 4 which is curved, and is adapted to be anchored above the sealing member 11, and in particular above its part that is anchored to step 21. With an insertion movement of vial 4 into the connecting component 105, or vice versa, the flexible coupling member 116 may widen slightly, by deforming elastically, so as to allow the insertion and attachment of vial 4 to the connecting component 105. Once such an attachment has occurred, the connecting component 105 and vial 4 are not separable from each other with an axial separation movement.

The connecting component 105 is also shaped so as to be able to be easily gripped by a user. In particular, a gripping portion 123 is provided where the user can place two fingers, such as index and middle fingers, to push the spike with the thumb towards vial 4, as will be further described. The gripping portion 123 is formed by a curved surface towards the interior below the upper edge 45. Preferably, the upper edge 151 extends along edge 35 of the flexible bag 1 by a length comprised between 60% and 100% of the extension of edge 35. This provides an optimal grip since the gripping portion 123 is sufficiently large.

Spike 107 is provided with an axial hole 126 so as to define an axial passage, and has a central body 129 and a head 112, opposite to tip 130. Head 112 is substantially flat and has greater radial extension than the central body 129 of spike 107. Head 112, which is the largest portion of spike 107, serves for supporting a finger, such as the thumb or the thenar of the hand, for pushing the spike through membrane 125 and cap 8 into vial 4, thereby opening a two-way flow of the diluent towards the interior of vial 4 and then of the solution again into the flexible bag 1. In the rest configuration, spike 107 is arranged completely into the flexible bag 1. In particular, it is partially inserted axially in the tubular collar 124. Its tip 130 faces towards the uncovered central portion 71 of cap 8. Moreover, spike 107 cannot slide axially towards the interior of the flexible bag 1 as it is provided with at least one stop, such as a flexible tab 131, which abuts against a corresponding step portion 132 of the tubular collar 124. In particular, tab 131, starting from the central body 129 of spike 107, is spaced apart from the latter in increasing manner with its extension towards the central part of the flexible bag 101.

Also in this embodiment, a sterile chamber 170 is provided between the connecting component 105 and vial 4, delimited by O-ring 110.

In order to provide a better understanding of the invention, a use of device 100 for reconstituting the drug contained in vial 4 by means of the liquid contained in the flexible bag 1 will now be described. The man skilled in the art will understand that the use of device 200 of the second embodiment is similar.

Figure 3:
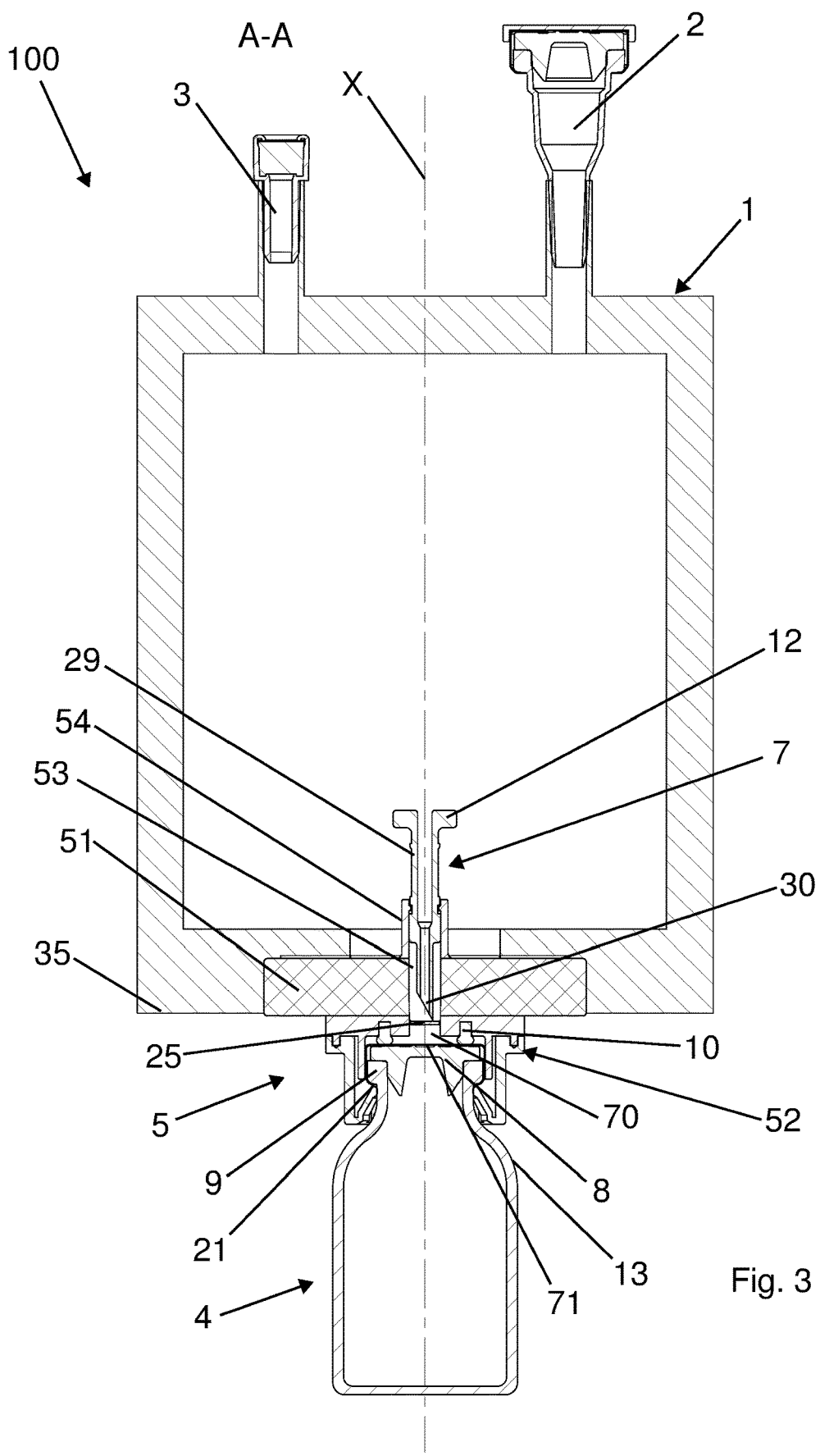
FIG. 3 shows section A-A of the device in FIG. 1 in rest position.
Figure 7:
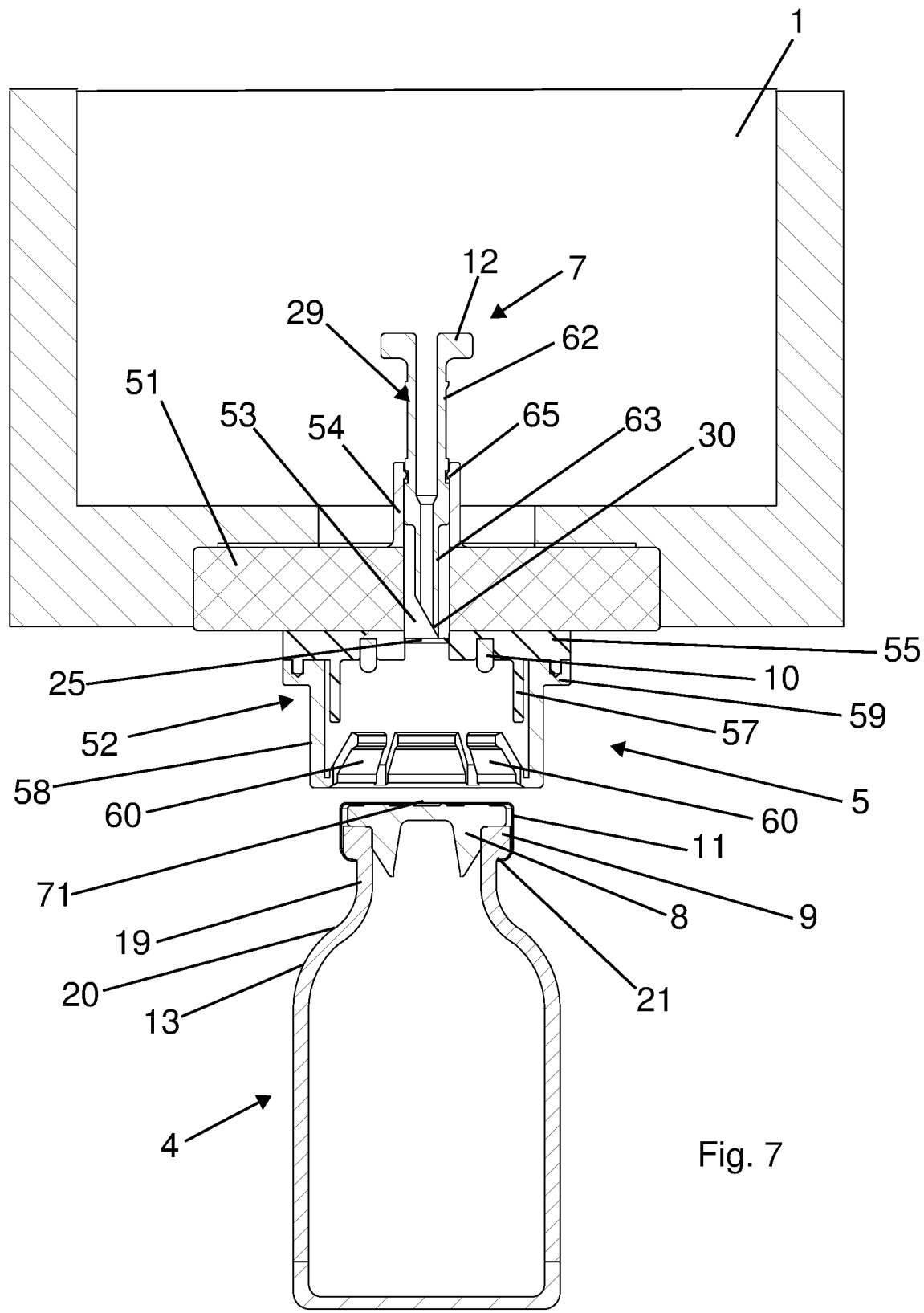
FIG. 7 is similar to FIG. 4, with the vial separated from the connecting component.
Figure 10:
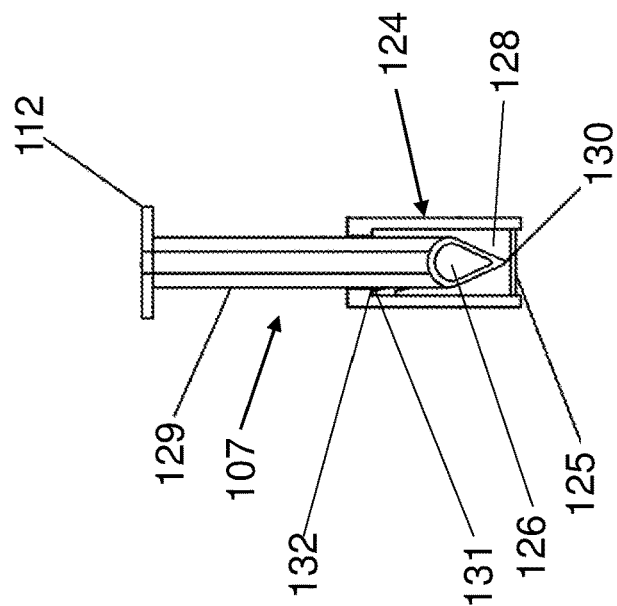
FIG. 10 shows a detail of the device in FIG. 9.
Figure 9:
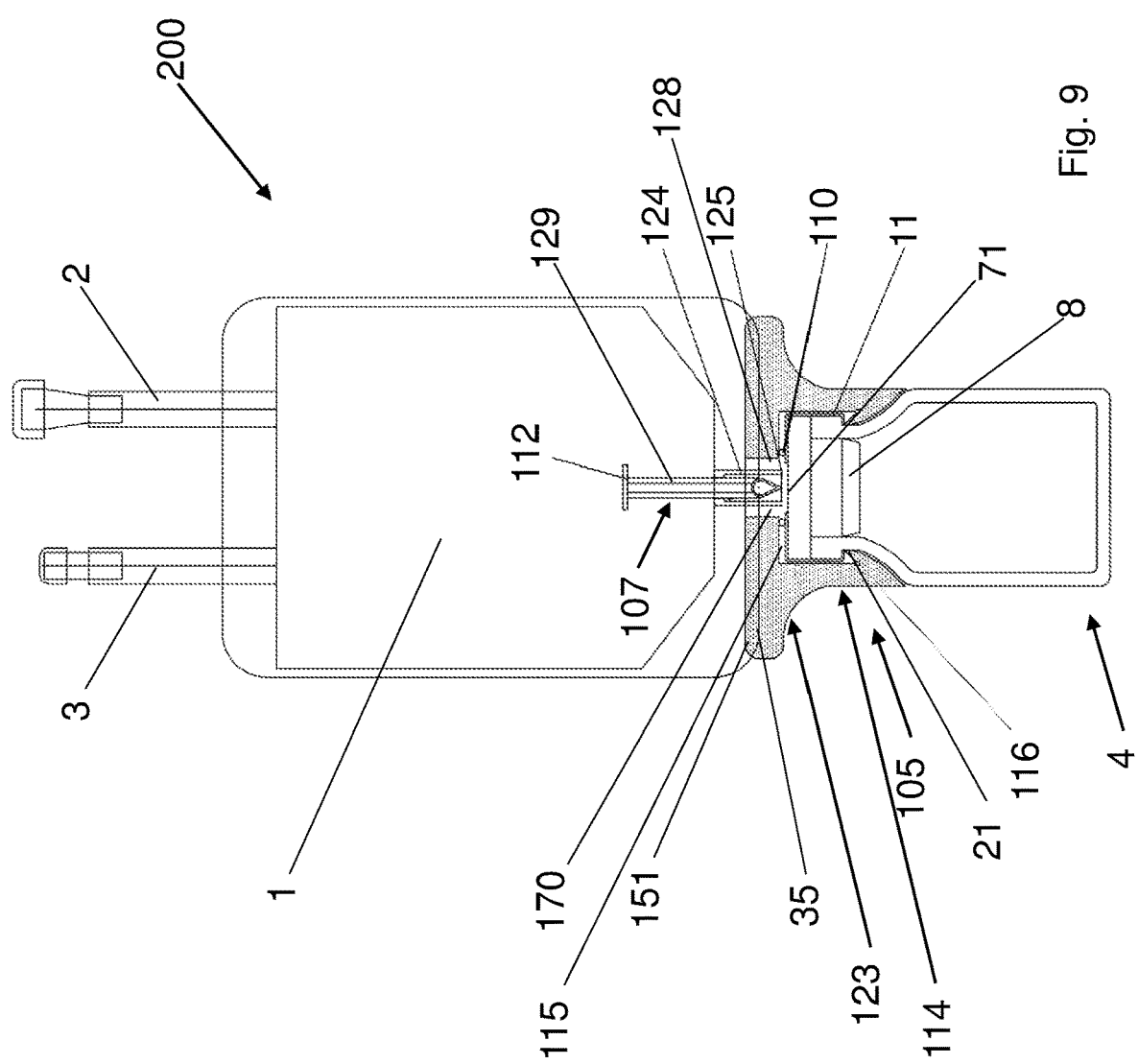
FIG. 9 shows a sectional view of a device of a second embodiment of the invention.

Device 100 is provided with spike 7 arranged inside, preferably completely inside, the flexible bag 1 in a configuration defined as "rest position", shown in FIG. 3.

In this configuration, an operator can grip the connecting component 5 with one hand, for example by placing the index finger and the middle finger at the lower surface of the upper portion 51 of the connecting component 5. Spike 7 is made to slide towards vial 4 by pushing it with the thumb or thenar of the hand, going beyond projection 65. The positioning of the thumb, which is in contact with the outer wall of the flexible bag 1, is provided above head 12 of spike 7. Spike 7 pierces membrane 25 first, then cap 8, crossing the sterile chamber 70. Preferably, the sliding of spike 7 stops when head 12 does in abutment against the tubular collar 54. In this configuration (FIG. 8), the diluent can pass from the flexible bag 1 to vial 4, escaping from the lumen of spike 7 at tip 30. Once reconstituted, the drug is in solution with the diluent. The solution can be transferred into the flexible bag 1, making it pass through spike 7. In order to facilitate the transfer of the solution from vial 4 to the flexible bag 1, the device should be held with vial 4 at the top and the flexible bag 1 at the bottom. An overpressure is created into vial 4 by exerting a pressure on the flexible bag 1 from the outside, such as a compression. The overpressure will force the solution towards the flexible bag 1. Using ports 2 or 3, the solution may be administered. This second configuration (shown in FIG. 8), in which spike 7 is partially inside vial 4, is defined as "working position". Therefore, by exerting a pressure on head 12 of spike 7, spike 7 is adapted to switch from the resting position, in which the spike is inside the flexible bag 1, to the working position, in which spike 7 is partially inside vial 4.

Advantageously, especially due to the presence of the sterile chamber 70, the sterility of the reconstituted drug during and after reconstitution is ensured. In fact, the solution is produced in a closed system, provided by device 100, so the sterility is not interrupted and the solution with the reconstituted drug is sterile. The sterile chamber 70 also ensures that spike 7 which penetrates into the vial is still sterile and is never exposed to the external environment.

Further advantages of the device of the invention include the elimination of errors of combination of active ingredient and diluent; the remarkable simplification of the manual operations for preparing the solution, eliminating the risk of injury by the staff involved and lowering of labor costs; a stable connection of the flexible bag with the vial; the possibility of reconstituting highly unstable solutions immediately before administration, allowing the patient to receive a top quality drug, since the process of degradation of the drug is minimized.

According to another aspect, the invention also provides a process for assembling a device 100 or 200 described above.

The device of the invention may be obtained by a process comprising the steps of a) sterilizing vial 4 and the flexible bag 1, provided with the connecting component 5, by exposure to UV rays;

b) assembling vial 4 to the connecting component 5 of the flexible bag 1 in a sterile environment, defining the sterile chamber 70 delimited by the closing member 8 of vial 4, by the connecting component 5 and by the sealing ring 10.

The attachment between the flexible bag 1 and the connecting component preferably occurs by heat welding.

The attachment between vial 4 and connecting component 5 preferably occurs by snap-fitting by means of a robot.

The connecting component 5, and thus also spike 7, and the outer surface of vial 5 are suitably sterilized. For example, the sterilization may be obtained by exposure to UV-C rays. The assembly takes place in a sterile environment.

Alternatively, the components may be assembled in a non-sterile environment and sterilization may be carried out by means of an electron beam to obtain the sterile chamber 70, This operation is carried out at the factory.

In this case, the process comprises the steps of a) fixing the flexible bag 1 to the connecting component 5;

b) fixing the vial 4 to the connecting component 5, defining a chamber 70 delimited by the closing member 8 of vial 4, by the connecting component 5 and by the sealing ring 10, c) sterilizing chamber 70 by means of electron beam sterilization.

In both cases, it is preferable to check the correct attachment of vial 4 to the connecting component 5.

After having provided an exemplary description of embodiments of the invention, some clarifications are provided to prevent the invention from being misinterpreted or interpreted in a limiting manner. In particular, it is clear that terms such as "upper", "lower", "upwards", "internally" and the like are used for descriptive purposes in a conventional manner and referring to the accompanying figures.

The invention claimed is:

1. A device for reconstituting an active ingredient in the form of sterile powder, comprising:

a vial containing said active ingredient as sterile powder having a mouth, a neck and a pierceable closing member which closes the mouth; an annular step being present between the mouth and the neck;

a flexible bag containing a sterile liquid;

a connecting component fixed to the vial and to the flexible bag;

an axially perforated spike, constrained to the connecting component and adapted to pierce the closing member, said axially perforated spike comprising a tip, facing towards the closing member, and a head opposite to the tip, said axially perforated spike being inserted in a hole of the connecting component, a pierceable membrane sealing the hole of the connecting component;

a sealing member sealing the closing member at the mouth and being anchored to said annular step, said sealing member having an open central portion and being arranged so as to leave a central portion of the closing member uncovered;

an elastomeric sealing ring arranged between the connecting component and the closing member of the vial and in contact with the sealing member, with at least a portion of the sealing ring being received in an annular groove provided on the connecting component, wherein there is provided a hermetically sealed, empty sterile chamber, delimited by the closing member, by the connecting component and by the elastomeric sealing ring, the hermetically sealed sterile chamber delimited at a top thereof by the pierceable sealing membrane and by the connecting component, laterally by the elastomeric sealing ring, and at a bottom thereof by a part of an upper side of the sealing member and by the uncovered central portion of the closing member;

wherein the connecting component is provided with a plurality of coupling teeth which fix the connecting component to the vial, the coupling teeth being in abutment against the portion of the sealing member that covers said annular step of the vial so that the elastomeric sealing ring is subjected to compression, so as to ensure hermetic sealing of the sterile chamber;

wherein the axially perforated spike is adapted to slide from a rest position inside the flexible bag to a working position, piercing the pierceable sealing membrane before crossing the hermetically sealed sterile chamber and piercing the closing member when a pressure is exerted on the head with at least one finger of a hand, allowing the passage of the sterile liquid from the flexible bag to the vial, and of the reconstituted active ingredient from the vial to the flexible bag, whereby the active ingredient is reconstituted in sterile conditions.

2. A device according to claim 1, wherein the connecting component is provided with a tubular collar arranged inside the flexible bag, and wherein the axially perforated spike is at least partially inserted into the tubular collar.

3. A device according to claim 1, wherein said head of the axially perforated spike is larger than the rest of the axially perforated spike.

4. A device according to claim 1, wherein the axially perforated spike is provided with first coupling means and the connecting component is provided with second coupling means constrained to the first coupling means in said rest position, so as to prevent undesired axial slidings of the axially perforated spike.

5. A device according to claim 1, wherein the connecting component is welded to the flexible bag.

6. A device according to claim 1, wherein the connecting component comprises an elongated gripping portion, whereby the axially perforated spike is adapted to be pushed towards the vial applying a force thereon with a finger of the a hand and simultaneously gripping the elongated gripping portion with two other fingers of the hand.

7. A device according to claim 1, wherein the connecting component comprises an annular projection in contact with a lateral surface of the sealing member.

8. A device according to claim 1, comprising one or more ports for the administration of the reconstituted active ingredient.

9. A process for obtaining a device according to claim 1, comprising the steps of:
a) sterilizing the vial and the flexible bag, provided with the connecting component, by exposure to UV rays;
b) assembling the vial to the connecting component of the flexible bag in a sterile environment, defining the hermetically sealed sterile chamber delimited by the closing member of the vial, by the connecting component and by the sealing ring.

10. A process for obtaining a device according to claim 1, comprising the steps of:
a) fixing the flexible bag to the connecting component;
b) fixing the vial to the connecting component, defining a chamber delimited by the closing member of the vial, by the connecting component and by the elastomeric sealing ring,
c) sterilizing the chamber by means of electron beam sterilization to obtain said hermetically sealed sterile chamber.

* * * * *